United States Patent [19]

Schwan

[11] 4,115,387

[45] Sep. 19, 1978

[54] 3-METHYL-4-PHENYL-1,2,3,4-TETRAHYDROBENZ [H]ISOQUINOLINE HYDROBROMIDE

[75] Inventor: Thomas J. Schwan, Norwich, N.Y.

[73] Assignee: Morton-Norwich Products, Inc., Norwich, N.Y.

[21] Appl. No.: 854,550

[22] Filed: Nov. 25, 1977

[51] Int. Cl.$^2$ ............................................. C07D 217/02
[52] U.S. Cl. ............................ 260/286 R; 260/283 R; 424/258

[58] Field of Search ....................... 260/283 CF, 286 R

[56] References Cited

U.S. PATENT DOCUMENTS 3,940,400  2/1976  Schwan .......................... 260/283 CF Primary Examiner—Donald G. Daus
Assistant Examiner—D. B. Springer
Attorney, Agent, or Firm—Anthony J. Franze

[57] ABSTRACT

The title compound is useful as an anthelmintic agent.

1 Claim, No Drawings

3-METHYL-4-PHENYL-1,2,3,4-TETRAHYDROBENZ [H]ISOQUINOLINE HYDROBROMIDE

This invention is concerned with the compound 3-methyl-4-phenyl-1,2,3,4-tetrahydrobenz[H]-isoquinoline hydrobromide.

This compound is useful as an anthelmintic agent. When administered per os by gavage in a suspension at a dose of about 300 mg/kg to mice harboring *Hymenolepis nana*, an 84% reduction in worm population is secured.

The method currently preferred for the preparation of the compound of this invention follows:

A. 2-(1-Naphthylmethylamino)-1-phenyl-1-propanol hydrochloride

A mixture of 78.0 g (0.50 mole) of 1-naphthaldehyde, 50.5 g (0.50 mole) triethylamine, 93.5 g (0.50 mole) of 2-amino-1-phenyl-1-propanol hydrochloride, and 500 ml $CH_3OH$ was stirred and refluxed for 45 min., then cooled to 15°-20° while 14.0 g (0.38 mole) of sodium borohydride was added over 30 min. The reaction mixture was stirred at ambient temperature for 30 min. and diluted with 700 ml $H_2O$. The mixture was stirred for 60 min. and extracted with 600 ml $CHCl_3$ followed by 100 ml $CHCl_3$. The combined organic extracts were washed with 200 ml $H_2O$, dried ($MgSO_4$), and concentrated to dryness in vacuo to give 129 g of the free base of the product.

Treatment of a 30.5 g (0.105 mole) sample of the free base dissolved in ethanol with ethanolic hydrogen chloride gave 22.8 g (66%) of the product, m.p. 204°-206°. An analytical sample, m.p. 204°-206°, was obtained by recrystallization from isopropanol.

Anal. Calcd. for $C_{20}H_{21}NO \cdot HCl$ C, 73.27; H, 6.77; N, 4.27; Found: C, 72.98; H, 6.79; N, 4.20.

B. 3-Methyl-4-phenyl-1,2,3,4-tetrahydrobenz[H]isoquinoline hydrobromide

To 98.0 g (0.337 mole) of the free base of A was added cautiously 500 ml 48% HBr. The mixture was stirred and heated to reflux temperature over one hour. After an 18 hr. reflux period, the mixture was stirred in an ice bath for one hour, the solid filtered through a medium sintered glass funnel, air dried for three hrs., washed with 2 × 150 ml portions of ethyl acetate, and air dried for one hour. The product weighed 93.3 g (78%) and melted at 336°-342°. The analytical sample, m.p. 330°-336°, was obtained by recrystallization from methanol.

Anal Calcd. for $C_{20}H_{19}N \cdot HBr$: C, 67.80; H, 5.69; N, 3.95; Found: C, 67.69; H, 5.89; N, 3.88.

What is claimed is:

1. The compound 3-methyl-4-phenyl-1,2,3,4-tetrahydrobenz[H]-isoquinoline hydrobromide.